United States Patent [19]

Vermeire

[11] Patent Number: 5,004,475
[45] Date of Patent: Apr. 2, 1991

[54] HIP PROSTHESIS

[76] Inventor: Dirk V. Vermeire, Pierrelaan 19, B-2160 Brecht, Belgium

[21] Appl. No.: 445,854
[22] PCT Filed: Mar. 15, 1989
[86] PCT No.: PCT/BE89/00011
§ 371 Date: Jan. 12, 1990
§ 102(e) Date: Jan. 12, 1990
[87] PCT Pub. No.: WO89/08436
PCT Pub. Date: Sep. 21, 1989

[30] Foreign Application Priority Data

Mar. 15, 1988 [BE] Belgium .............................. 8800297

[51] Int. Cl.[5] .............................................. A61F 2/36
[52] U.S. Cl. ......................................... 623/23; 623/16
[58] Field of Search .......................... 623/22, 23, 18, 16

[56] References Cited

U.S. PATENT DOCUMENTS

| 4,031,571 | 6/1977 | Heimke et al. | 623/23 |
| 4,310,931 | 1/1982 | Muller | 623/23 |
| 4,659,067 | 4/1987 | Fournier | 623/23 |
| 4,714,470 | 12/1987 | Webb, Jr. et al. | 623/23 X |
| 4,728,334 | 3/1988 | Spotorno | 623/23 |

FOREIGN PATENT DOCUMENTS

| 0027159 | 4/1981 | European Pat. Off. . |
| 0176421 | 4/1986 | European Pat. Off. . |
| 0202908 | 11/1986 | European Pat. Off. . |
| 2295730 | 12/1975 | France . |
| 2419717 | 10/1979 | France . |
| 2548533 | 1/1985 | France . |
| 2555902 | 6/1985 | France . |
| 2029229 | 12/1982 | United Kingdom . |
| 2142830 | 12/1986 | United Kingdom . |
| 2203943 | 11/1988 | United Kingdom . |

Primary Examiner—Ronald Frinks
Attorney, Agent, or Firm—Renner, Otto, Boisselle & Sklar

[57] ABSTRACT

A femoral hip prosthesis and a stem therefor comprising a femur end to be received in the femur and a head end for connection to a hip head, which stem is provided for medial support on the public arch ($S_1$) with a curved, smooth medial stem support part, is provided for lateral support on the lateral cortex ($S_2$) with a lateral stem support part, and is provided for lateral support on the greater trochanter ($S_3$) with a lateral comb-like stem support part located between the lateral stem support part and the head end and comprising a number of combs, the combs connecting onto the lateral side protruding laterally relative thereto, and which stem is provided on the ventral and dorsal sides at the point of the metaphysial portion with at least one groove which consists of groove portions converging in the direction of the head end and enclosing an apex.

18 Claims, 3 Drawing Sheets

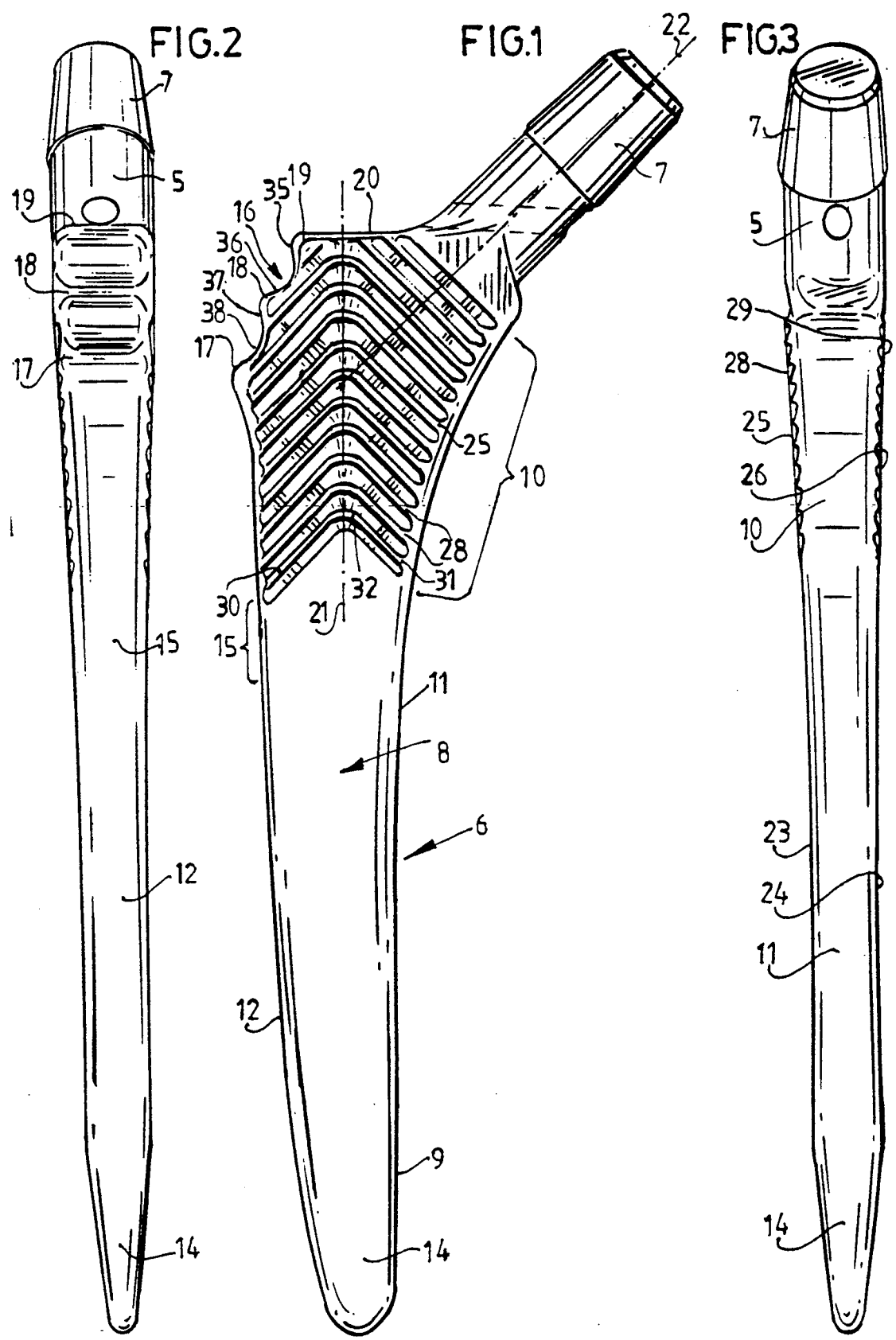

HIP PROSTHESIS

The present invention relates to a femoral hip prosthesis in general and more particularly to a stem for a femoral prosthesis which can be arranged in the femur without cement.

BACKGROUND AND SUMMARY OF THE INVENTION

Visible in the metaphysis of a normal hip is a pattern of support and traction trabeculae, which pattern corresponds with the pattern of mechanical forces. In the course of extensive research a prosthesis has been developed possessing a form such that the natural bio-geometrical forces pattern is approximated as closely as possible in the femur metaphysis. In other words the femoral prosthesis must be arranged in the femur such that during loading the centre of gravity of the femoral prosthesis lies as closely as possible to or coincides with the metaphysial centre point.

FIGS. 5, 6 and 7 in the drawing are femur sections showing different supporting possibilities of the femoral prosthesis, whereby for the sake of clarity the contact surfaces are shown enlarged and shaded.

In FIG. 5 the prosthesis 2 arranged in the femur 1 supports medially on the pubic arch ("Adamse boog") $S_1$ and laterally on the cortex $S_2$. In the case of unipodal loading G of the hip head 3 the centre of gravity CG will come to lie during the resolution of forces very close the pubic arch $S_1$ and at a large interval from the metaphysial centre CM. The overpressure created at the pubic arch $S_1$ has to be compensated by for instance a flange supporting against the greater trochanter 4.

In the situation shown in FIG. 6 the prosthesis 2 supports medially on the pubic arch $S_1$ and laterally on the greater trochanter $S_3$. When unipodal loading G occurs the centre of gravity CG is located in the neck 5 of the prosthesis and once again at an interval from the metaphysial centre.

FIG. 7 shows the ideal loading according to the invention, whereby the prosthesis 2 supports medially on the pubic arch $S_1$ and laterally on the lateral cortex $S_2$ and the greater trochanter $S_3$. In the case of unipodal loading G the centre of gravity CG and the metaphysial centre CM now coincide. It is the loading shown in FIG. 7 which is approximated as closely as possible with the prosthesis according to the invention.

It is noted that the loadings of the femur 1 shown in FIGS. 5-7 have been confirmed in mechanical loading experiments with plastic prosthesis elements, whereby, using polarised light the forces/loading pattern was visualised.

The invention relates to a stem for a hip prosthesis and the hip prosthesis itself, which stem is provided for medial support on the pubic arch ($S_1$) with a curved, smooth medial stem support part, is provided for lateral support on the lateral cortex ($S_2$) with a lateral stem support part, and is provided for lateral support on the greater trochanter ($S_3$) with a lateral comb-like stem support part located between the lateral stem support part and the head end and comprising a number of combs, the comb connecting onto the lateral side protruding laterally relative thereto, and which stem is provided on the ventral and dorsal side at the point of the metaphysial portion with at least one groove which consists of groove portions converging in the direction of the head end and enclosing an apex. Achieved through this manner of supporting is that the centre of gravity of the prosthesis coincides with or lies in the direct vicinity of the metaphysial centre, and in this way duplicates as closely as possible the natural bio-geometrical forces in the femoral metaphysis.

For the lateral supporting on the greater trochanter $S_3$ it is favourable that the comb-shaped stem support part comprises a number of combs and that the comb connecting onto the lateral side protrudes laterally relative thereto. This comb-like structure for the stem support part prevents a distal sliding of the prosthesis when loading occurs, after ingrowth into the bone of the greater trochanter, while in addition excessive loading of the lateral cortex $S_2$ is countered and therefore the rotation moment in the case of unipodal loading.

The stem is provided on the ventral and dorsal side at the point of the metaphysial portion with at least one groove. These grooves contribute to the anchoring of the prosthesis in the femoral metaphysis. The form of the grooves corresponds with that of the natural support and traction trabeculae. During driving of the prosthesis into the femur released trabecular structures moreover accumulate in the grooves, particularly at the point of the apex, and form ventral and dorsal strips of bone which contribute to a rapid anchoring of the prosthesis in the femur. Since the ventral and dorsal side surfaces of the stem diverge from one another towards the head end at the height of the grooves, a distal sliding of the prosthesis when loading occurs is prevented.

It is favourable if the radius of curvature of the curved medial stem support part amounts to 120-150 cm is preferably 130-140 cm and more preferably 135 cm. The prosthesis thus supports on the medial calcar and the meta-diaphysial portion of the femur, and this preferably over a length of approximately 10 cm.

For a good balance between the medial supporting on the pubic arch $S_1$ and the lateral supporting on the cortex $S_2$ it is favourable that in the direction towards the femur end a flat medial side portion connects onto the curved medial stem support part, which portion diverges relative to the flat lateral side facing away from it, whereby in preference the angle of divergence amounts to 1°-5°, is preferably 2°-4° and more preferably 3°. It is thus possible that the prosthesis supports laterally on the meta-diaphysial a transition, i.e. on the point where the cortex of the femur has its highest diameter, and the supporting takes place over a length of approximately 3 cm.

The stem preferably possesses a substantially rounded rectangular section. An unnatural loading of the femoral diaphysis is thus avoided. Were the diaphysis to come into complete contact with the prosthesis stem there would then occur a stiffening in the elasticity of the femoral diaphysis, which can have negative effects on the anchoring on the lateral cortex.

At least the metaphysial portion of the stem is preferably coated with hydroxyapatite. This hydroxyapatite coating contributes to an accelerated and improved ingrowth of the bone. Because mainly the metaphysial portion of the stem is in contact with the femur, at least this portion of the stem has to be coated with hydroxyapatite.

Finally, it is remarked that the prosthesis has a form such that in the case of a femur break or as a result of other unexpected circumstances the prosthesis is easy to remove without causing any great damage to the femur.

Mentioned and other features of the hip prosthesis and hip prosthesis stem according to the invention will be elucidated hereinafter on the basis of the description of an embodiment of the prosthesis, which is given only by way of example, while reference is made to the annexed drawing.

BRIEF DESCRIPTION OF THE DRAWING

FIGS. 1-3 are ventral, lateral and medial views respectively of the prosthesis according to the invention;

FIGS. 1-3 show an embodiment of the femoral prosthesis 6 according to the invention which possesses an external form such that after arrangement in femur 1 the prosthesis 6 supports medially on the pubic arch $S_1$, and laterally on the lateral cortex $S_2$ on the one side and on the greater trochanter $S_3$ on the other (see FIG. 4). The prosthesis 6 comprises a hip head 3 which can be arranged on the head end 7 of the prosthesis stem 8 which is received with its femur end 9 in the femur 1.

Figure 4:
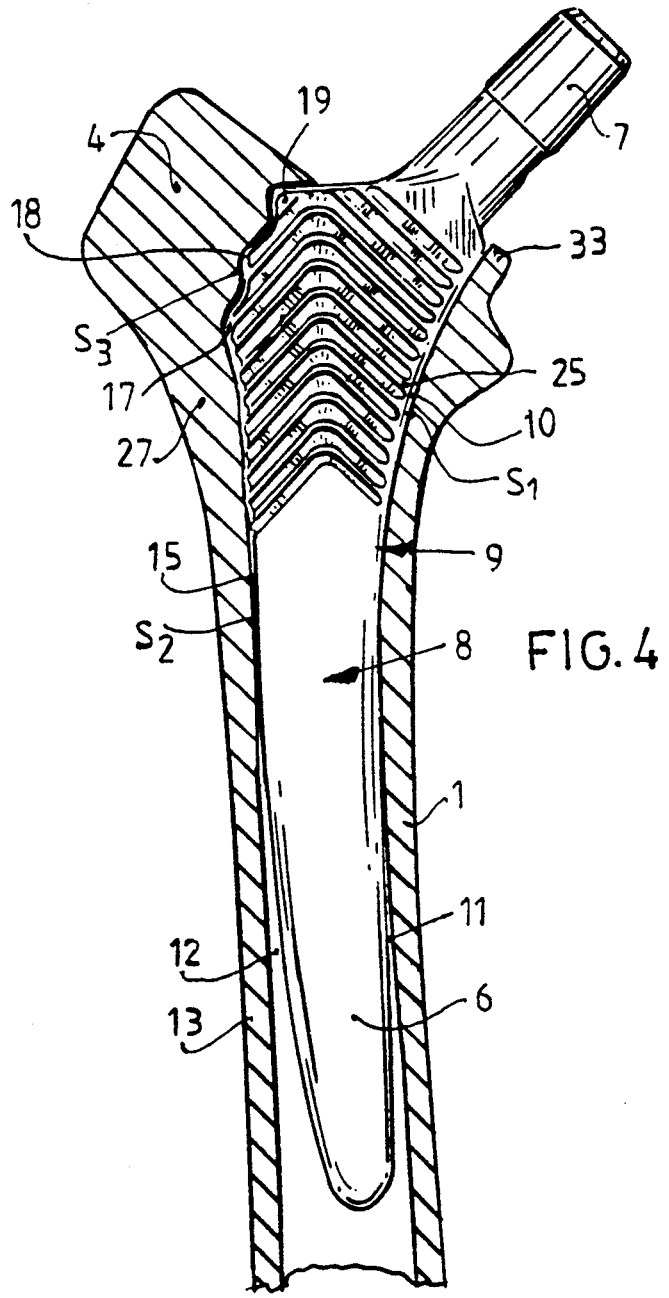
FIG. 4 is a view with the femur in section of the prosthesis from FIG. 1 arranged in the femur.
Figure 5:
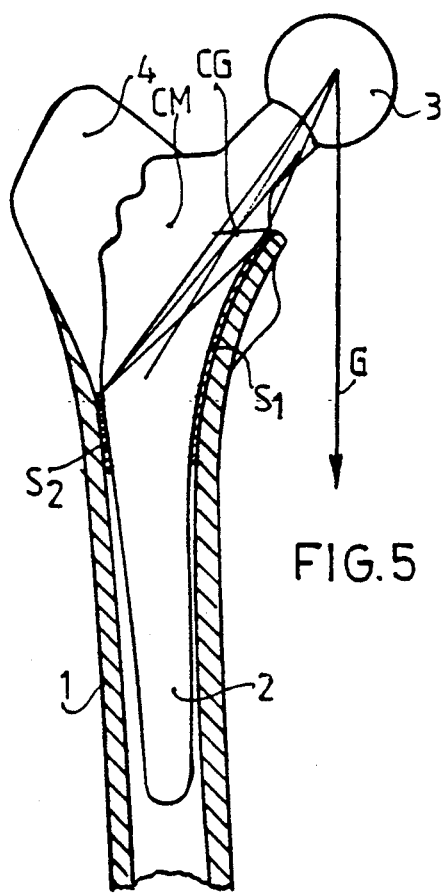
FIGS. 5-7 are femur sections showing different supporting possibilities of the femoral prosthesis, wherein for the sake of clarity the contact surfaces are shown enlarged and shaded.
Figure 6:
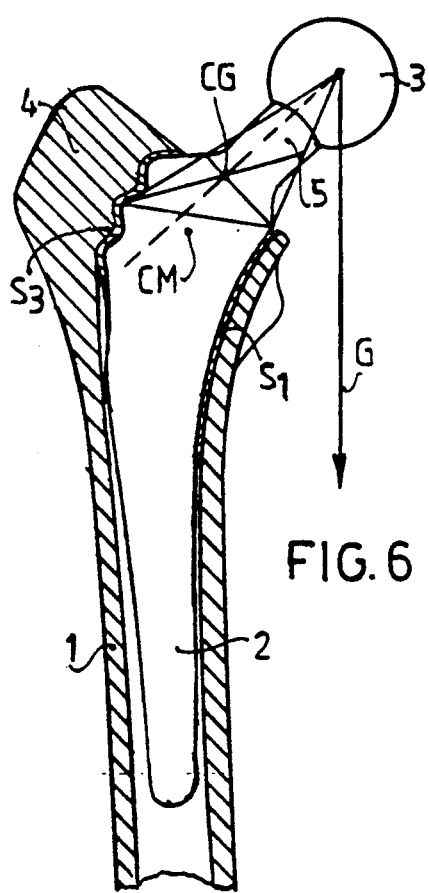
Figure 7:
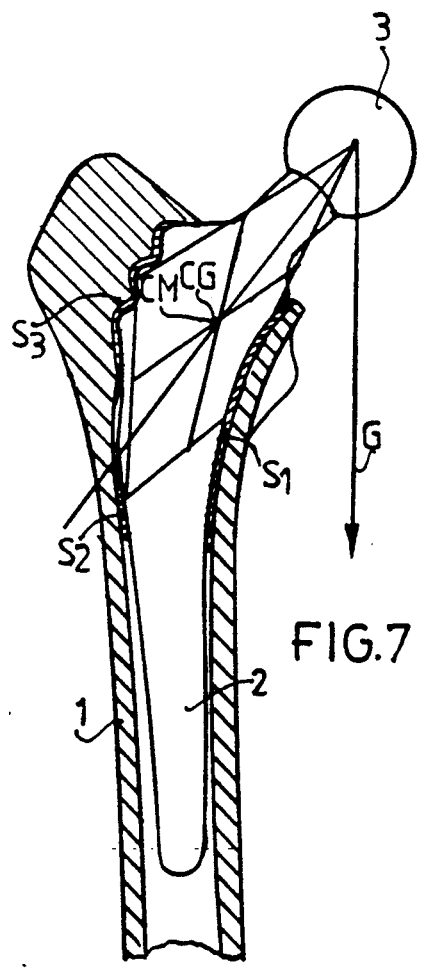

The stem is provided with a curved smooth medial support part 10 which supports on the pubic arch $S_1$. The radius of curvature of the medial support part 10 amounts to 120-150 cm is preferably 130-140 cm, and in the case of prosthesis 6 is 135 cm. This curvature is chosen such that a physiological CCD angle remains as far as possible preserved. The length of the medial support part surface amounts to circa 10 cm. Connecting onto the curved medial stem support part 10 in the direction of the femur end 9 is a flat medial side part 11 which diverges relative to the flat lateral side 12 facing away from it at an angle of divergence of 1°-5°, preferably 2°-4°, and for prosthesis 6, 3°. The flat lateral side part 11 and the flat lateral side part 12 make substantially no contact with the femur diaphysis 13 so that the above mentioned stiffening in the elasticity of the diaphysis does not occur. The femur end 9 ends in a rounded point 14 which acts during arrangement of the prosthesis 6 in the femur 13 as guiding member.

The flat lateral side 12 transposes into the lateral stem support part 15 which supports on the lateral cortex $S_2$ at the point of the meta-diaphysial transition. This lateral stem support surface has a length of about 3 cm.

Lying on the lateral side between the lateral stem support part 15 and the head end 7 is the comb-shaped stem support part 16 comprising in the case of prosthesis 6 three laterally protruding combs 17-19. The combs lie after arrangement in the femur in the greater trochanter 4. The comb 19 originates in a surface 20 lying perpendicular to the longitudinal axis 21 of stem 8, which axis 21 encloses an angle of circa 135° with the longitudinal axis 22 of the neck 5, and transposes to a surface 35 lying perpendicular thereto. This surface 35 transposes into a virtually horizontal surface 36 of the comb 18, after which a downward curved surface 37 transposes into an outward curved surface 38 which determines the laterally protruding comb 17, and transposes into the lateral side surface 12.

The ventral side 23 and the dorsal side 24 diverge to an increasing extent towards the neck 5 whereby the divergence is maximal in the respective side portions 25 and 26 which come to lie in the femoral mataphysis 27. These portions 25 and 26 are provided with grooves 28 and 29. The grooves 28 and 29 possess groove portions 30 and 31 converging towards the head end 7 and enclosing an apex 32. In these groove portions 30 and 31 loose trabecular tissue is guided to the apex 32 where the tissue accumulates and strips of bone furthering intergrowth form. For a good supply of tissue the grooves 28 and 29 connect on one side to the curved medial stem support part 10 and on the other side to the lateral stem support part 15 or comb-shaped stem support part 16.

Through the divergence of the lateral and medial sides 11 and 12 on the one hand and the ventral and dorsal sides 23 and 24 on the other the stem 8 acquires a rounded rectangular section which mainly furthers contact at the point of the metaphysis and lessens contact in the diaphysis.

The arrangement of the femoral hip prosthesis 2, 6 according to the invention takes place as follows. The natural hip head is sawn off to about 1 cm above the lesser trochanter 33, whereby care is taken that the bone structure at the point of the trochanter remains as intact as possible. The spongelike bone is subsequently removed over a depth of approximately 2 cm. Using a rasp the pubic arch and the medial cortex are filed down. Laterally, only spongelike tissue is removed at the point of the meta-diaphysial transition.

The lateral portion of the femur neck is then removed with nipper pliers and the spongy tissue is destructured from the greater trochanter with a chisel in order to obtain a good adaptation to the combs 17-19 of the prosthesis.

After removal of the rasp a prosthesis 2, 6 according to the invention corresponding to the shape of the rasp is driven into the femur. If the lateral arches of the prosthesis disappear into the femur spongy tissue can still be added. It is important that the point of the trochanter must be situated at the height of the centre of the head of the femoral prosthesis. Washing is then carried out with physiological water and rivocine in order to remove loose material. The arranging of the drain and the closing of the wound are performed in conventional manner.

What is claimed is:

1. Stem for a hip prosthesis having a femur end to be received in the femur and a head end for connection to a hip head, which stem is provided for medial support on the pubic arch ($S_1$) with a curved, smooth medial stem support part, is provided for lateral support on the lateral cortex ($S_2$) with a lateral stem support part, and is provided for lateral support on the greater trochanter ($S_3$) with a lateral comb-like stem support part located between the lateral stem support part and the head end and comprising a number of combs, the comb connecting onto the lateral side protruding laterally relative thereto, and which stem is provided on the ventral and dorsal side at the point of the metaphysial portion with at least one groove which consists of groove portions converging in the direction of the head end and enclosing an apex.

2. Stem as claimed in claim 1, characterized in that the radius of curvature of the curved medial stem support part amounts to 120-150 cm.

3. Stem as claimed in claim 1, characterized in that in the direction towards the femur end a flat medial side portion connects onto the curved medial stem support part, which portion diverges relative to the flat lateral side facing away from it.

4. Stem as claimed in claim 3, characterized in that the angle of divergence amounts to 1°14 5°.

5. Stem as claimed in claim 3, characterized in that the angle of divergence amounts to 2°14 4°.

6. Stem as claimed in claim 3, characterized in that the angle of divergence amounts to 3°.

7. Stem as claimed in claim 1, characterized in that the groove connects on the one side to the curved medial stem support part and on the other side to the lateral stem support part or the comb-like stem support part.

8. Stem as claimed in claim 1, characterized in that the stem possesses a substantially rounded rectangular section.

9. Stem as claimed in Claim 1 characterized in that at least the metaphysial portion of the stem is coated with hydroxyapatite.

10. Hip prosthesis comprising a stem as claimed in claim 1 and a hip head connected to said stem.

11. Stem as claimed in claim 2, characterized in that the radius of curvature of the curved medial stem support part amounts to 130–140 cm.

12. Stem as claimed in claim 11, characterized in that the radius of curvature of the curved medial stem support part amounts to 135 cm.

13. Stem as claimed in claim 2, characterized in that in the direction towards the femur end a flat medial side portion connects onto the curved medial stem support part, which portion diverges relative to the flat lateral side facing away from it.

14. Stem as claimed in claim 2, characterized in that the groove connects on the one side to the curved medial stem support part and ont he other side to the lateral stem support part or the comb-like stem support part.

15. Stem as claimed in claim 11, characterized in that in the direction towards the femur end a flat medial side portion connects onto the curved medial stem support part, which portion diverges relative to the flat lateral side facing away from it.

16. Stem as claimed in claim 12, characterized in that in the direction towards the femur end a flat medial side portion connects onto the curved medial stem support part, which portion diverges relative to the flat lateral side facing away from it.

17. Stem as claimed in claim 11, characterized in that the groove connects on the one side to the curved medial stem support part and on the other side to the lateral stem support part or the comb-like stem support part.

18. Stem as claimed in claim 12, characterized in that the groove connects on the one side to the curved medial stem support part and on the other side to the lateral stem support part or the comb-like stem support part.

* * * * *